(12) United States Patent
Jordan et al.

(10) Patent No.: US 7,563,582 B2
(45) Date of Patent: Jul. 21, 2009

(54) PROCESS FOR SCREENING CHEMICAL COMPOUNDS FOR MODULATING THE INTERACTION OF AN EVH1 DOMAIN AND A PROCESS FOR DETECTING SAID INTERACTION

(75) Inventors: Birgit Jordan, Hattersheim (DE); Peter Drückes, Freiburg (DE); Thomas Jarchau, Würzburg (DE); Ulrich Walter, Veitshöchheim (DE)

(73) Assignee: sanofi-aventis Deutschland GmbH, Frankfurt am Main (DE)

( * ) Notice: Subject to any disclaimer, the term of this patent is extended or adjusted under 35 U.S.C. 154(b) by 510 days.

(21) Appl. No.: 09/989,188

(22) Filed: Nov. 21, 2001

(65) Prior Publication Data
US 2002/0136717 A1    Sep. 26, 2002

(30) Foreign Application Priority Data
Nov. 25, 2000 (DE) .................................. 10058596

(51) Int. Cl.
*G01N 33/53* (2006.01)
*G01N 33/535* (2006.01)
(52) U.S. Cl. .......................... 435/7.1; 435/5; 424/141.1
(58) Field of Classification Search ............... 435/4, 435/7.1, 7.4, 7.72, 7.9, 7.94; 530/300
See application file for complete search history.

(56) References Cited

U.S. PATENT DOCUMENTS 5,262,299 A * 11/1993 Evangelista et al. ............ 435/6

FOREIGN PATENT DOCUMENTS

| WO | WO 97/29373 | 8/1997 |
| WO | WO 98/01755 | 1/1998 |
| WO | WO 98/15830 | 4/1998 |
| WO | WO 01/74858 | 10/2001 |
| WO | WO 01/96594 | 12/2001 |

OTHER PUBLICATIONS

Reinhard, Matthias et al., *Guidebook to the Cytoskeletal and Motor Proteins*, Oxford University Press, pp. 168-171 (1999).
Reinhard, Matthias et al., "Identification, purification, and characterization of a zyxin-related protein that binds the focal adhesion and microfilament protein VASP (vasodilator-stimulated phosphoprotein)", Proc. Natl. Acad. Sci. USA, vol. 92, pp. 7956-7960 (1995).
Reinhard, Matthias et al., "VASP interaction with vinculin: a recurring theme of interactions with proline-rich motifs", FEBS Letters, vol. 399, pp. 103-107 (1996).
Jarchau, Thomas, et al., "Purification and assays of vasodilator-stimulated phosphoprotein", Methods in Enzymology, vol. 298, pp. 103-113 (1998).
Niebuhr, Kirsten, et al., "A novel proline-rich motif present in ActA of *Listeria monocytogenes* and cytoskeletal proteins is the ligand for the EVH1 domain, a protein module present in the Ena/VASP family", The EMBO Journal, vol. 16, No. 17, pp. 5433-5444 (1997).
Bader et al., A cGMP-dependent Protein Kinase Assay for High Throughput Screening Based on Time-Resolved Fluorescence Resonance Energy Transfer, *J. Biomol. Screen.* 6:255-64 (2001).

* cited by examiner

*Primary Examiner*—Stacy B Chen (57) ABSTRACT

The invention relates to processes for identifying chemical compounds which are capable of modulating the interaction between VASP and zyxin. VASP or a VASP derivative and zyxin or a zyxin derivative which interact with one another are brought into contact with a chemical compound to be examined. The effect on the interaction can be determined using antibodies against VASP or a VASP derivative and/or zyxin or a zyxin derivative, or with the aid of fluorescent labels on VASP or a VASP derivative and zyxin or a zyxin derivative.

14 Claims, 5 Drawing Sheets

SEQUENCE LISTING

<160> NUMBER OF SEQ ID NOS: 3

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      illustrative peptide

<400> SEQUENCE: 1

Phe Pro Pro Pro Pro
 1               5

<210> SEQ ID NO 2
<211> LENGTH: 5
<212> TYPE: PRT

-continued

```
<213> ORGANISM: Artificial Sequence
<220> FEATURE:
<223> OTHER INFORMATION: Description of Artificial Sequence: Synthetic
      binding peptide

<400> SEQUENCE: 2

Trp Pro Pro Pro Pro
 1               5

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      motif peptide

<400> SEQUENCE: 3

Ala Pro Pro Pro Pro
 1               5
```

PROCESS FOR SCREENING CHEMICAL COMPOUNDS FOR MODULATING THE INTERACTION OF AN EVH1 DOMAIN AND A PROCESS FOR DETECTING SAID INTERACTION

This invention relates to processes for identifying a chemical compound capable of modulating the interaction of an EVH1 domain or a protein having an EVH1 domain with an EVH1 binding domain or a protein having an EVH1 binding domain. The invention further relates to processes for identifying a chemical compound capable of modulating the interaction between VASP or a VASP derivative and zyxin or a zyxin derivative, and to a process for detecting this interaction.

The interaction of proteins through EVH1 domains and EVH1 binding domains plays an important role in signal transduction pathways. These pathways are involved in the adhesion of cells to tissue surfaces, their motility, the change of the morphology of cells, their aggregation, and particularly to the activation of platelets and lymphocytes. Such processes may contribute to the genesis and the progression of a large number of diseases, such as inflammatory disorders, disorders of the blood vessels, the cardiovascular system and its organs, or neoplastic cell and tissue changes, such as cancer.

A large number of proteins contain an EVH1 domain or an EVH1 binding domain. For example, zyxin is a protein having an EVH1 binding domain, whereas VASP is a protein having an EVH1 domain. The domain of a protein is a three dimensional region of a protein or a protein surface that may be formed by a plurality of sections of a peptide chain, which may fold independently, as a compact region.

An EVH1 (Ena-VASP homology) domain is based on a highly conserved sequence section of a length of about 115 amino acids that is present in all proteins of the Ena-VASP family. It is responsible for their correct subcellular localization through interactions with the respective EVH1 binding proteins. The EVH1 domain comprises seven β-pleated sheets and a C-terminal α-helix, which are folded to a characteristic β-barrel structure. They have a high structural similarity to and homology with pleckstrin and to phosphotyrosine binding domains.

In the various EVH1 binding proteins, the EVH1 domains of the Ena/VASP protein family recognize proline-rich peptide sequences having an FPPPP (SEQ. ID. NO. 1) core motif, which are folded in the form of a polyproline helix of type II. EVH1 binding proteins having such FPPPP (SEQ. ID. NO. 1) sequence motifs are, for example, the cytoskeleton-associated proteins zyxin and vinculin or the surface protein ActA of the facultative intracellular bacterium *Listeria monocytogene*. Owing to the interaction of the EVH1 domains of VASP and the FPPPP (SEQ. ID. NO. 1) motifs in the EVH1 binding domain of zyxin, there is an interaction between zyxin and VASP.

The abbreviation VASP denotes a 'vasodilator-stimulated phosphoprotein'. VASP is expressed in almost all mammalian cells, where it is a substrate of cAMP- and cGMP-dependent protein kinases. VASP, and proteins homologous to VASP, form the Ena/VASP protein family. Proteins homologous to VASP include, for example, the Ena protein in *Drosophila* and the Mena and Evl proteins in the mouse. In humans, particularly high concentrations of VASP are found in cardiovascular cells, platelets, endothelial cells, smooth muscle cells, and neointima cells.

In cultivated cells, VASP is associated with cell-matrix contact sites (focal adhesion points), cell-cell contacts, and the actin filament system and dynamic membrane structures, for example, the midline of motile cells. A large amount of experimental data confirms that VASP provides profilactin, an adapter molecule, to sites with the cytoskeletal proteins zyxin and vinculin or with the surface protein ActA in cells infected with *Listeria* spec. The EVH1 domain binding FPPPP (SEQ. ID. NO. 1) motif in the proteins zyxin, vinculin and ActA and the EVH1 domain in VASP have been characterized functionally and structurally by NMR structure elucidation.

Functional studies confirm that VASP is a decisive factor for increased localized formation of actin filament. Thus, it is an important factor for the regulation of cell adhesion and cell motility, wherein VASP interacts directly with other proteins such as zyxin, vinculin or profilin. This was demonstrated, for example, by microinjection of peptides which contain the binding motif of the VASP-zyxin interaction. The VASP field is reviewed in Guidebook to the Cytoskeletal and Motor Proteins (Eds., Kreis, T., and Vale, R.), Oxford University Press, (1999) at pp. 168-171. For these reasons, the complex between VASP and zyxin is considered to be a novel potential target structure which can be used for influencing disorders associated with pathological changes in cell adhesion and cell motility. For example, arteriosclerosis and coagulation disorders and the associated cardiovascular disorders may be treated with appropriate medicaments for modulating this interaction. Accordingly, VASP and zyxin or homologues or derivatives of these proteins which interact with one another can be used, inter alia, to identify chemical substances which can be used as therapeutically active compounds for treating cardiovascular disorders.

A method is known for detecting the interaction between an EVH1 binding domain, such as that contained in zyxin, with an EVH1 domain, such as that contained in VASP. This method comprises a radioactive solid-phase assay or overlay assay, wherein zyxin is detected by radioactively labeled VASP following its transfer to a solid phase with or without prior gel-electrophoretic separation. Reinhard et al. PNAS 92, 7956-7960, 1995; Reinhard et al. FEBS Lett. 399,103-107,1996. Owing to its format and the radioactive detection, this process is not suitable for a detection method with high-throughput screening (HTS). The radioactive labeling method used limits the scope of use. Furthermore, the complicated separating steps encountered in gel-electrophoretic separation does not allow its use in automated screening processes and can cause problems with the specificity of the detection.

WO 98/01755 discloses non-human VASP-like proteins (Mena, Evl). These proteins are of limited suitability for constructing a screening model. This is because they only represent the target structure to be constructed for pharmaceutical screening (preferably human components), to a certain degree.

The use of lanthanide chelates as fluorescent labels and the use of time-resolved fluorescence measurement using these fluorescent labels, for example for HTS, is disclosed by Wallac Oy (Finland) in WO 97/29373 and WO 98/15830. To date, no results have been published on the use of fluorescent labels for analyzing the interaction between an EVH1 binding domain, such as that contained in zyxin, with an EVH1 domain, such as that contained in VASP, which are suitable for use in screening processes.

Accordingly, it is an object of the present invention to develop a screening process for identifying chemical compounds capable of modifying the interaction between an EVH1 binding domain, such as that contained in zyxin, or a protein having an EVH1 binding domain, with an EVH1 domain for example, that contained in VASP, or a protein having an EVH1 domain. This screening process should be suitable for high throughput screening, and should be safe, fast, highly specific and reliable, even when operated automatically. Furthermore, in this screening process, a target structure relevant for pharmaceutical screening should be constructed, preferably with human components.

The invention further relates to a process for identifying a chemical compound which modulates an interaction between an EVH1 binding domain or a protein having an EVH1 binding domain with an EVH1 domain or a protein having an EVH1 domain, which process comprises:

a) bringing an EVH1 binding domain or a protein having an EVH1 binding domain which interacts with an EVH1 domain or a protein having an EVH1 domain into contact with a chemical compound to be examined. "Bringing into contact" is to be understood as meaning the steps of 1) coating a support with a domain, 2) blocking and washing, 3) adding the other domain (with or without test substance), and 4) incubation up to and including washing;

b) incubating the mixture according to a) with an antibody which specifically binds to an EVH1 binding domain or a protein having an EVH1 binding domain or an EVH1 domain or a protein having an EVH1 domain or which has an antigen which is fused with or chemically coupled to these domains or proteins;

c) incubating the mixture according to b) with an antibody which is capable of specifically binding the antibody from mixture b) and to which a label is attached which can be detected biochemically or physiochemically; and d) detecting the label on the antibody after incubation according to c) by biochemical or physicochemical detection.

Modulation of the interaction may result in stronger binding of the binding partners or a weakening of this binding. Stronger binding of the binding partners is evident, for example, by a mutually increased affinity of the domains or proteins involved. An increased affinity can be noticed by reduced affinity constants of the binding partners involved. The affinity constants can be determined using standard methods of biochemistry. Such methods are disclosed, for example, in Pingoud, A., Urbanke, K., Arbeitsmethoden der Biochemie; 1997; Gruyter Lehrbuch or in Wilson, K., Goulding, K. H., Methoden der Biochemie; 1991; Thieme flexible Taschenbücher. This applies analogously to a weakening of the binding of the binding partners. A protein having an EVH1 binding domain is a protein which contains an EVH1 binding domain. Likewise, a protein having an EVH1 domain is a protein which contains an EVH1 domain.

In a preferred embodiment, the above-described process for identifying a chemical compound is carried out on a surface which consists of a solid body. Accordingly, the process is referred to as a solid-phase assay. In a preferred embodiment, the surface of the solid body is coated with an EVH1 binding domain or a protein having an EVH1 binding domain, which interacts with an EVH1 domain or a protein having an EVH1 domain. In a further preferred embodiment, the surface of the solid body is coated with an EVH1 domain or a protein having an EVH1 domain which interacts with an EVH1 binding domain or a protein having an EVH1 binding domain. The surfaces coated in this manner can then be coated with a reagent or protein which is inert with respect to the interaction examined, such as bovine serum albumin. The chemical compound to be examined, which may be dissolved in an aqueous organic solvent, is then applied to the coated surface.

The solid body may be made of various materials such as plastic, glass or metal. Preferably, the solid body consists of an organic polymer. In a further embodiment, the solid body consists of a chemical material which is insoluble in or resistant to organic solvents, acids, bases or aqueous solutions. The solid body may have various shapes. In a preferred variant, for example, it may be present as a microtiter plate, an Eppendorf vessel, a glass tube, a film, or a microchip. The solid body may consist of one material or component or a plurality of materials or components.

Coating of the surface of the solid body with an EVH1 binding domain or a protein having an EVH1 binding domain that interacts with an EVH1 domain or a protein having an EVH1 domain can be carried out directly on the solid body. In the case of solid bodies composed of different materials, it is also possible to coat a carrier material separately from a solid base. The coated carrier material can then be applied to this solid base, to form a solid body comprising the coated carrier material and solid base.

The surface may be initially coated with an EVH1 binding domain or a protein having an EVH1 binding domain. This domain or protein can interact with an EVH1 domain or a protein having an EVH1 domain added in a second step. Alternatively, the surface can be initially coated with an EVH1 domain or a protein having an EVH1 domain. The interaction with an EVH1 binding domain or a protein having an EVH1 binding domain is then established by adding this domain or protein, in a second step.

To coat the surface of the solid body with an EVH1 binding domain, a protein having an EVH1 binding domain, an EVH1 domain, or a protein having an EVH1 domain, the surface of the solid body is incubated with one of these domains or proteins. Likewise, to establish the interaction between an EVH1 binding domain or a protein having an EVH1 binding domain and an EVH1 domain or a protein having an EVH1 domain, one domain or a protein having this domain is incubated with the other domain or a protein having this other domain. The excess of non-interacting domains or proteins having these domains is then removed by washing. Incubation means that proteins and surface are brought into contact with one another for a defined period of time at a fixed temperature and at certain buffer and ion concentrations. To this end, the proteins can be present dissolved or suspended in buffered aqueous media containing chemical additives.

The protein having an EVH1 binding domain is preferably zyxin or a zyxin derivative. In principle, any protein having an EVH1 binding domain can be used for the processes of the present invention. The EVH1 binding domain can also be employed when physically separated from other components of a protein, as an isolated domain or as EVH1 binding peptide. The EVH1 binding domain used can be, for example, an EVH1 binding domain as contained in zyxin or a zyxin derivative. The protein having an EVH1 domain is preferably VASP or a VASP derivative. In principle, any protein having an EVH1 domain can be used. The EVH1 domain can also be present when physically separated from other components of a protein, as isolated domains. The EVH1 domain used can, for example, be an EVH1 domain as contained in VASP.

The VASP or VASP derivative, zyxin or zyxin derivative can be the corresponding proteins or parts thereof, from any species. Preference is given to using VASP and zyxin or parts thereof of mouse vertebrae and more particularly, human vertebrae. Amino acid sequences of VASP are disclosed at Swissprot under P50552 (human) and at EMBL under X98475.1 (mouse). Amino acid sequences of zyxin are disclosed at Swissprot under Q15942 (human) and under Q62523 (mouse). The required proteins can be isolated from the corresponding vertebrae tissues or cells, for example, from platelets. They can also be prepared recombinantly in host cells or microorganisms such as insect cells or *E. coli* cells, and subsequently purified. Recombinant VASP can be purified from insect cells using immuno affinity chromatography, as described in detail in Jarchau, T., Mund, T., Reinhard, M., U. Walter (1998) Purification and Assays of Vasodilator-Stimulated Phosphoprotein. Methods in Enzymology Vol. 298, 103-113. The EVH1 domain of VASP or the EVH1 binding domain of zyxin can be purified recombinantly from *E. coli* as glutathione S-transferase fusion proteins, as described in detail in Current Protocols in Molecular Biology, ed.: F. M. Ausubel, Wiley-Interscience (1987).

In one embodiment, the protein having an EVH1 binding domain is a zyxin derivative. The zyxin derivative generally consists of a fusion protein of glutathione S-transferase which has the first 142 amino acids of the N-terminus of zyxin fused to its C-terminus. In principle, the glutathione S-transferase used can be the amino acid sequence of any species. Preference, however, is given to using sequences from man, mouse, rat or *Schistosoma japonicum*. Such sequences are disclosed, for example, at Swissprot under P08263 (human), P24472 (mouse), and P04904 (rat). Suitable fusion partners for the first 142 C-terminal amino acids of zyxin, in addition to glutathione S-transferase, are hexahistidine, thioredoxine or maltose binding protein.

In another embodiment, a process for identifying a chemical compound which modulates an interaction between an EVH1 binding domain or a protein having an EVH1 binding domain with an EVH1 domain or a protein having an EVH1 domain is carried out using a surface which consists of a solid body which is coated with domains or proteins as described above and which forms part of a microtiter plate.

For carrying out the process of the present invention for the specific detection of the EVH1 binding domain, a protein having an EVH1 binding domain, the EVH1 domain, or a protein having an EVH1 domain, it is possible to use monoclonal or polyclonal antibodies. The monoclonal or polyclonal antibodies must have binding specificity for one of these domains or proteins, or to an antigen fused to or chemically coupled with these domains or proteins.

In one embodiment, a monoclonal antibody with binding specificity for VASP or zyxin is used for carrying out the process according to the invention. Such an antibody can be synthesized using hybridoma cells and then concentrated and purified. The cultivation of hybridoma cells, the production of antibodies with the aid of hybridoma cells, their purification and concentration is carried out by standard methods, as described, for example, in Current Protocols in Immunology, ed.: J. E. Coligan, Wiley-Interscience (1991). This textbook also teaches methods for determining the binding specificity for an antigen. For the purposes of the processes of the present invention, the antigen used can be an EVH1 binding domain or a protein having an EVH1 binding domain, for example zyxin or a zyxin derivative, or an EVH1 domain or a protein having an EVH1 domain, for example VASP or a VASP derivative. The antigen may also be an antigen fused with these domains or proteins, such as glutathione S-transferase, hexahistidine, thioredoxine, maltose binding protein, or a chemically coupled antigen.

In a further embodiment, the antibody used for carrying out the process according to the invention is a polyclonal antibody which has binding specificity for an EVH1 binding domain, a protein having an EVH1 binding domain, such as zyxin or a zyxin derivative, an EVH1 domain or a protein having an EVH1 domain, such as VASP or a VASP derivative, or an antigen fused with these domains or proteins, such as glutathione S-transferase, hexahistidine, thioredoxine, maltose binding protein, or a chemically coupled antigen. Preparation, purification, testing and use of polyclonal antibodies is described in detail in Current Protocols in Immunology, ed.: J. E. Coligan, Wiley-Interscience (1991).

In preferred embodiments of the process of the present invention, the antibody having binding specificity for VASP is the monoclonal antibody mAB IE245 or the monoclonal antibody mAB IE273.

The secondary antibodies which specifically bind the primary antibodies of the present invention which have binding specificity for an EVH1 binding domain, a protein having an EVH1 binding domain, an EVH1 domain, a protein having an EVH1 domain, or an antigen fused to or chemically coupled with these domains or proteins, may carry a label that can be detected biochemically or physiochemically. A biochemically or physiochemically detectable label is, for example, an enzyme, a radioactive isotope or a fluorescent label. In preferred embodiments, the biochemically or physiochemically detectable label can be alkaline phosphatase or β-galactosidase, an isotope, such as a radioactive isotope, or a fluorescent label, in particular a lanthanide complex, such as a europium complex.

In yet another embodiment, a process of this invention, as described above, can be used for identifying a medicament. Such medicaments can be used for treating cardiovascular disorders, inflammatory disorders, disorders of the blood vessels, or for neoplastic cell and tissue changes, such as cancer.

The invention further relates to a chemical compound for modulating the interaction between an EVH1 binding domain or a protein having an EVH1 binding domain and an EVH1 domain or a protein having an EVH1 domain which was identified by a process of the present invention, as described above. Such chemical compounds are preferably peptides, in particular with the sequences FPPPP (SEQ. ID. NO. 1) or WPPPP (SEQ. ID. NO. 2), or their chemical derivatives and proline-rich homologues. Such chemical compounds can be medicaments for the treatment of the disorders described above.

In a preferred embodiment, the invention relates to the monoclonal antibody mAB IE245, which has binding specificity for VASP, and to hybridoma cells capable of producing the monoclonal antibody mAB IE245. In a further embodiment, the hybridoma cells capable of producing the monoclonal antibody mAB IE245 are from the strain DSM ACC2444.

In another preferred embodiment, the invention relates to the monoclonal antibody mAB IE273, which has binding specificity for VASP, and to hybridoma cells capable of producing the monoclonal antibody mAB IE273. In this embodiment, the hybridoma cells capable of producing the monoclonal antibody mAB IE273 are from the strain DSM ACC2445.

The hybridoma cells DSM ACC2444 and DSM ACC2445 have been deposited at the Deutsche Stammsammlung für Mikroorganismen, Mascheroder Weg 1b, D-38124 Braunschweig, Germany, on Feb. 2, 2000 in accordance with the rules of the Budapest Treaty.

The invention furthermore relates to a surface which consists of a solid body and is coated with an EVH1 binding domain or a protein having an EVH1 binding domain or with an EVH1 domain or a protein having an EVH1 domain.

The protein having an EVH1 binding domain is preferably zyxin or a zyxin derivative. Furthermore, the zyxin derivative is preferably formed by a fusion protein of zyxin, a zyxin fragment and a glutathione S-transferase, or of zyxin or a zyxin fragment and a maltose binding protein, or of zyxin or a zyxin fragment and hexahistidine. The protein having an EVH1 domain is preferably VASP or a VASP derivative, or a fusion protein of VASP or a VASP fragment, and glutathione S-transferase, maltose binding protein, or hexahistidine.

In a preferred embodiment, the EVH1 binding domain or the protein having an EVH1 binding domain interacts with an EVH1 domain or a protein having an EVH1 domain. To establish this interaction, with respect to the proteins having an EVH1 binding domain, zyxin or a zyxin derivative is preferred. For example, a fusion protein of zyxin or a zyxin fragment and glutathione S-transferase or of zyxin or a zyxin fragment and maltose binding protein, is used. With respect to the proteins having an EVH1 domain, preference is given to using VASP or a VASP derivative or a fusion protein of VASP or a VASP fragment and glutathione S-transferase or maltose binding protein.

The invention furthermore relates to a microtiter plate which contains a surface coated with an EVH1 binding domain or a protein having an EVH1 binding domain and an EVH1 domain or a protein having an EVH1 domain, in particular with zyxin, a zyxin derivative or VASP or a VASP derivative. The microtiter plate can have various numbers of wells. For example, the microtiter plate may contain 3, 6, 12, 24, 48, 96, 192, 384, 768, 1536, 3072 or more wells. In preferred embodiments, the microtiter plate contains 384 wells, 768 wells, or 1536 wells. Moreover, in the described embodiments, the surface of the present invention may also be a component of other apparatus, vessels or devices, such as Eppendorf vessels, tubes of various materials, in particular of plastic or glass, chip-like devices, and other apparatus, devices or containers.

The invention furthermore relates to a process for identifying chemical compounds capable of modulating an interaction between an EVH1 binding domain or a protein having an EVH1 binding domain and an EVH1 domain or a protein having an EVH1 domain, which process comprises:
  a) bringing an EVH1 binding domain or a protein having an EVH1 binding domain into contact with an EVH1 domain or a protein having an EVH1 domain in the presence of at least one chemical compound to be examined, where in each case a fluorescent dye which enables an energy transfer between an EVH1 binding domain or a protein having an EVH1 binding domain and an EVH1 domain or a protein having an EVH1 domain is coupled to the EVH1 binding domain or a protein having an EVH1 binding domain and/or to the EVH1 domain or a protein having an EVH1 domain; and
  b) spectroscopically determining the presence or absence of chemical compounds capable of modulating an interaction following incubation according to a).

In this process, the fluorescent dye used is preferably APC, Cy5, or a lanthanide complex, or a europium complex.

In this process, the protein having an EVH1 domain used is preferably VASP or a VASP derivative. The protein having the EVH1 binding domain used is preferably zyxin or a zyxin derivative. The zyxin derivative can be a fusion protein of zyxin or a zyxin fragment with a glutathione S-transferase or of zyxin or a zyxin fragment with maltose binding protein.

The interaction between an EVH1 domain or a protein having an EVH1 domain, in particular VASP or a VASP derivative, and an EVH1 binding domain or a protein having an EVH1 binding domain, in particular zyxin or a zyxin derivative, can be determined spectroscopically when certain fluorescent dyes are coupled both to an EVH1 domain or a protein having an EVH1 domain, in particular VASP or a VASP derivative, and to an EVH1 binding domain or a protein having an EVH1 binding domain, in particular zyxin or a zyxin derivative. These fluorescent dyes permit an energy transfer when, by complex formation of the proteins to which they are coupled, they are brought into sufficiently close spatial vicinity to each other. The fluorescent dyes used can be compounds which complement each other as energy donor and energy acceptor.

The energy donor is excited by electromagnetic radiation of a specific wavelength. The excitation energy can be transferred to the energy acceptor if it is in close vicinity with the energy donor. Emitting an electromagnetic radiation of a specific wavelength, the energy acceptor returns to its ground state. This energy emission takes place at a wavelength different from that of the excitation of the energy donor. If energy donor and energy acceptor are chosen appropriately, the energy transfer takes place at spectroscopically detectable wavelengths of electromagnetic radiation, preferably in the range of visible light. If energy donor and energy acceptor are coupled to an EVH1 domain or a protein having an EVH1 domain, in particular VASP or a VASP derivative, and an EVH1 binding domain or a protein having an EVH1 binding domain, in particular zyxin or a zyxin derivative, the interaction of these proteins or protein derivatives can be detected directly by spectroscopic means.

One can detect a chemical compound which modifies the interaction of an EVH1 domain or a protein having an EVH1 domain with an EVH1 binding domain or a protein having an EVH1 binding domain if it causes a spectroscopically detectable change in the energy transfer when it is brought into contact with the interacting proteins. The energy donors used can be certain fluorescent dyes, such as lanthanide complexes, or europium complexes. The energy acceptors used can be certain fluorescent dyes, such as APC or Cy5. Each energy donor or energy acceptor can be coupled to the EVH1 domain or a protein having an EVH1 domain, in particular VASP or a VASP derivative, or to an EVH1 binding domain or a protein having an EVH1 binding domain, in particular zyxin or a zyxin derivative.

When the process of the present invention is carried out, the interacting domains or the interacting proteins containing the different domains are provided either with a complimentary energy donor or energy acceptor. In order to determine the interaction spectroscopically, the energy donor and energy acceptor must be present simultaneously in the molecular complex which mediates the interaction. Coupling of energy donor or energy acceptor can in each case be produced directly, via covalent bonds, or indirectly, via antibodies or biotin-streptavidin. Such antibodies are commercially available.

The invention further relates to a process for producing a pharmaceutical preparation for modulating the interaction between an EVH1 binding domain or a protein having an EVH1 binding domain and an EVH1 domain or a protein having an EVH1 domain, where a compound is identified using a process according to one or more processes of this invention, and the compound is mixed with pharmaceutical excipients and/or pharmaceutical carriers and subsequently, if appropriate, brought into a pharmaceutical presentation form.

The invention is further illustrated, without limitation, by the following examples.

EXAMPLE 1

Determination of the Interaction of VASP with Zyxin or a Zyxin Derivative Using a Solid-phase Assay (DELFIA)

In the solid-phase assay, a binding partner (VASP or zyxin) was immobilized on the surface of a microtiter plate (MTP) (=coating). The unsaturated binding sites on the surface of the plastic were blocked, and the surface was then incubated with the respective other binding partners. After the incubation, excess unattached protein was removed in a washing step. Using suitable antibodies, it was now possible to detect and quantify the specifically bound protein. Here, it was possible to improve the signal-noise (S/N) ratio considerably by using lanthanide chelates as fluorescent labels for the antibodies and the measurement of the time-resolved fluorescence.

For the solid-phase assay, the best coating and incubation conditions were characterized. It was found that the zyxin component (GST-zyxin(1-142) or zyxin(1-142)) was highly suitable for coating the MTP. For detecting VASP specifically bound to the immobilized zyxin, it was possible to use monoclonal antibodies against VASP which can be detected using lanthanide-labeled antibodies against mouse IgGs (Wallac: DELFIA anti-mouse-Eu(N1)).

The current assay protocol comprised 5 incubation steps and 3 washing steps:
1. Incubation of the empty MTPs with GST-zyxin(1-142) (coating);
2. Blocking with BSA (bovine serum albumin);
3. Washing with PBS (wash buffer);
4. Incubation with VASP (ligand) (with and without test substances);
5. Washing with PBS;
6. Incubation with detection mix: α-VASP (monoclonal anti-VASP antibody)+α-mouse-Eu (europium-labeled anti-mouse antibodies from Wallac);
7. Washing with DELFIA wash solution; and
8. Release of the bound lanthanide complex and fluorimetric measurement.

When the reagents/proteins were selected, it was found that the recombinant human VASP protein with complete amino acid sequence obtained from insect cells (baculo VASP) had a significantly better signal/noise ratio than VASP or VASP domains which were expressed in and obtained from *E. coli*.

EXAMPLE 2

Properties of the VASP-zyxin Solid-phase (DELFIA) Assay

Figure 1A:
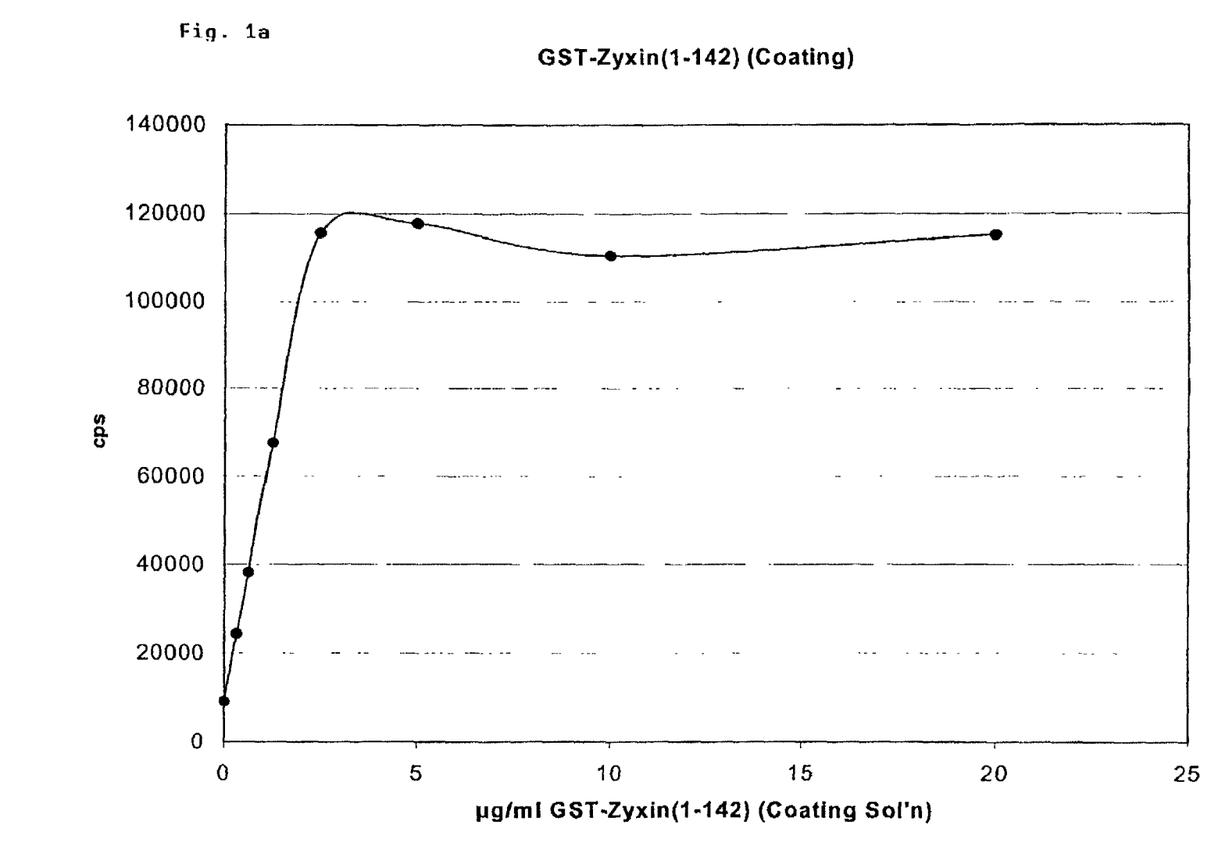
FIG. 1a: Coating of the MTPs with GST-zyxin(1-142): saturation is achieved at a coating solution concentration of 5 µg/ml.
Figure 1B:
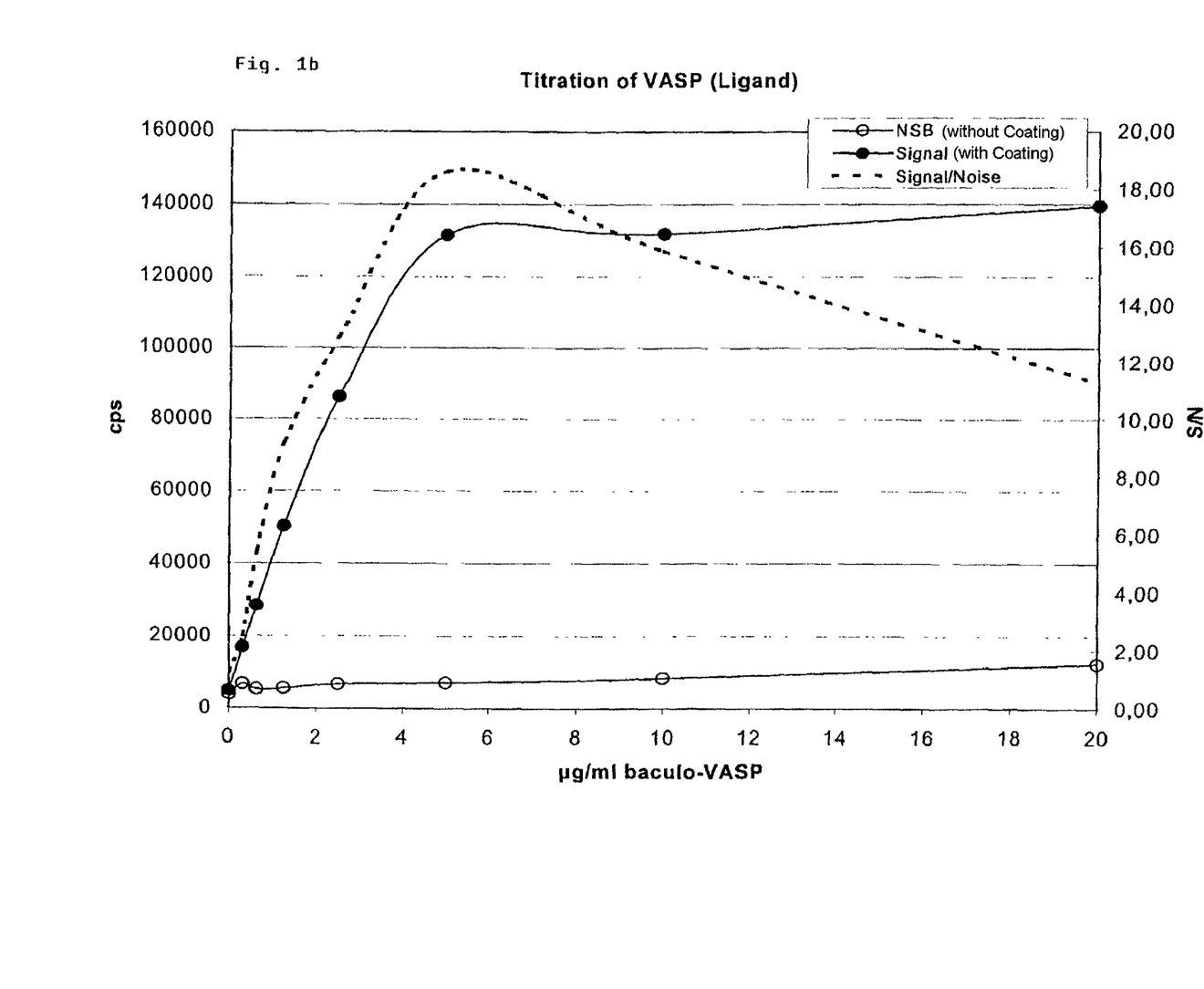
FIG. 1b: Coating of the MTPs with VASP: for incubations where the ligand used was VASP, a concentration of 5 µg/ml was found to give the best S/N ratio.

The optimum conditions for coating (GST-zyxin(1-142)) and ligand incubation (VASP) were determined by titrating the reagents. Saturation coating of the MTPs with GST-zyxin (1-142) was achieved with a coating solution concentration of 5 µg/ml (FIG. 1a). The volume per well used depended on the selected MTP format (50 µl or 100 µl for 96-well plates, 20 µl for 384-well plates). For incubations where the ligand was VASP, a concentration of 5 µg/ml was found to be the concentration with the best S/N ratio (FIG. 1b).

EXAMPLE 3

Detection

During further optimization of the assay, it was found that selection of the monoclonal antibody is of great importance for the detection of the bound VASP. Assays comprising the anti-VASP antibody IE273 had a S/N ratio of about one order of magnitude better than assays comprising the mAB IE245. The optimal amount of IE273 antibody to be employed was found to depend on the amount of VASP used earlier. An optimal S/N ratio was found with a molar ratio of IE273 to VASP of 1:16 (ratio by weight 1:4). For incubations with a concentration of 5 µg of VASP/ml, the best signal resulted when the detection was carried out using 1.25 µg of IE273/ml. This is also of importance in the context of the optimization or reduction of the washing steps, since it was found that the washing step between incubation with VASP and detection is important and must not be omitted.

EXAMPLE 4

Competition Experiments with Peptidergic Inhibitors

Figure 2:
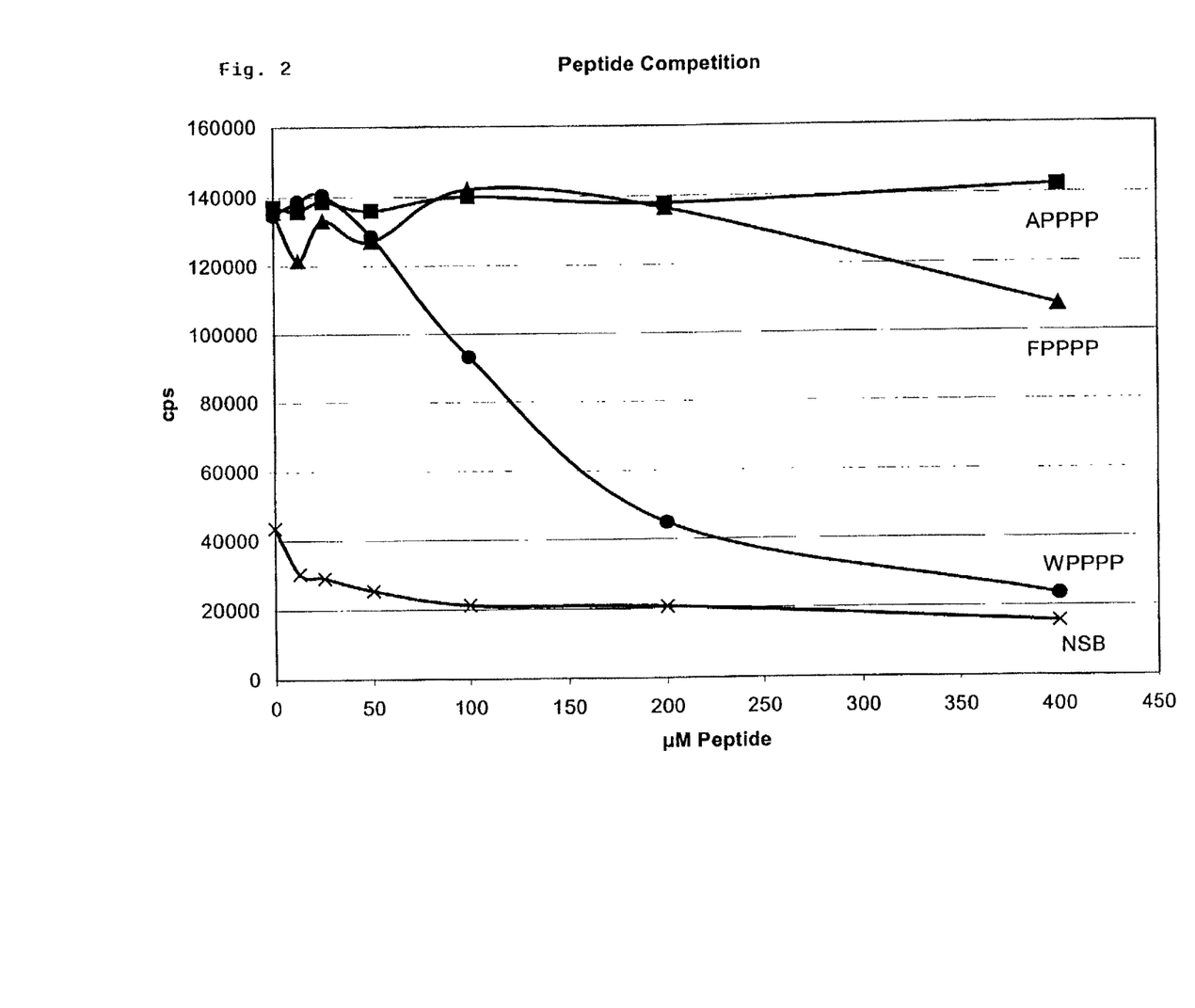
FIG. 2: Inhibition of the VASP/zyxin interaction by competing peptides containing the APPPP (SEQ. ID. NO. 3), FPPPP (SEQ. ID. NO. 1), or WPPPP (SEQ. ID. NO. 2) motif.

Thus far, there are no known non-peptidergic inhibitors of the VASP/zyxin interaction To simulate the action of potential inhibitors, inhibition experiments were carried out using competing peptides which contained the VASP binding motif of zyxin (FPPPP (SEQ. ID. NO. 1)). In earlier works (Niebuhr et al. (1997) EMBO J. 16, 5433) mutations in this motif and their effect on the inhibition of the VASP/ActA interaction, which is also based on the binding of VASP to FPPPP (SEQ. ID. NO. 1) motifs in ActA, were studied It was found that peptides having an APPPP (SEQ. ID. NO. 3) motif showed considerably worse inhibition when compared to the wild type sequence FPPPP (SEQ. ID. NO. 1), whereas peptides having a WPPPP motif had an even better inhibition that the wild type motif (inhibition: WPPPP (SEQ. ID. NO. 2)>FPPPP (SEQ. ID. NO. 1)>APPPP (SEQ. ID. NO. 3)). Zyxin peptides having corresponding mutations were used to compete with the VASP/zyxin interaction. For the apparent inhibition constants of the peptides, the same sequence was found as for the VASP/ActA interaction (FIG. 2): WPPPP (SEQ. ID. NO. 2)>FPPPP (SEQ. ID. NO. 1)>APPPP (SEQ. ID. NO. 3).

This showed that it is possible to influence the VASP/zyxin interaction by using competing substances and possibly novel inhibitors of a different type, which can be detected by the assay described.

EXAMPLE 5

Solvent Tolerances

Figure 3A:
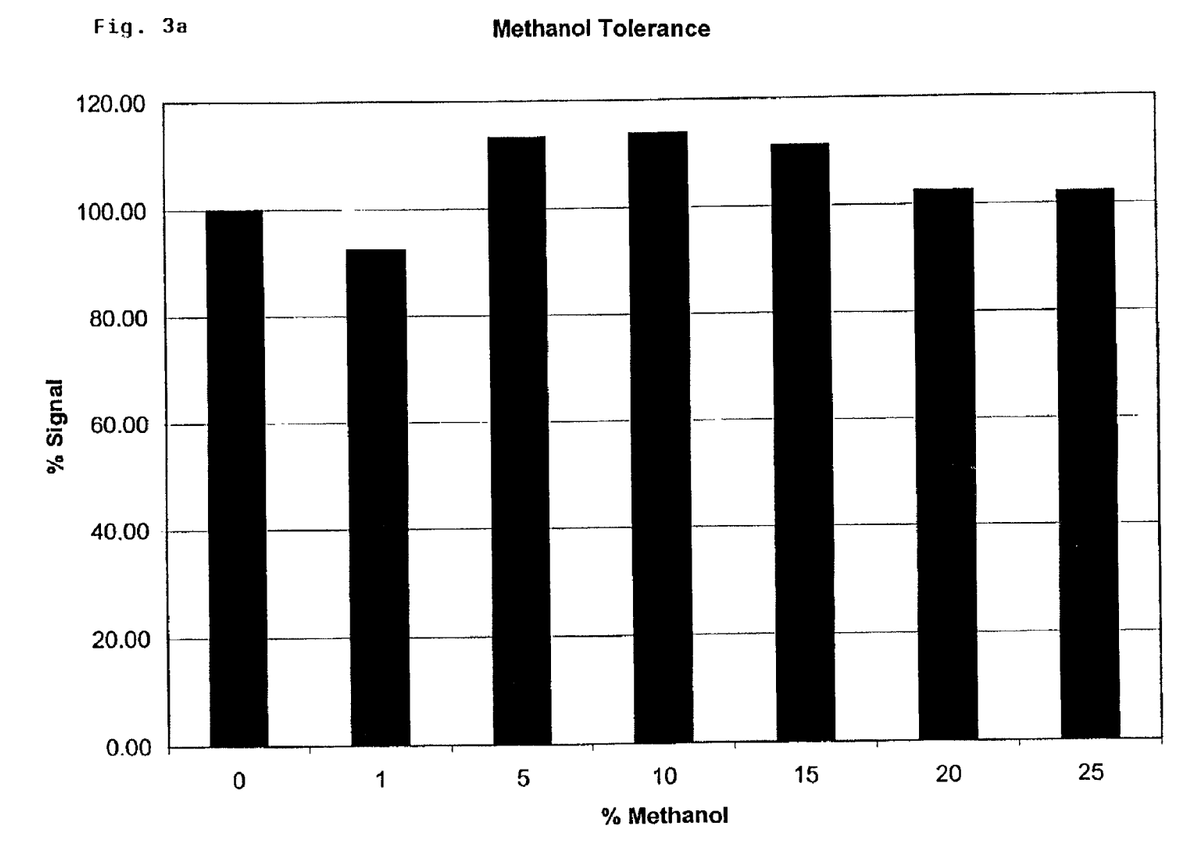
FIG. 3a: Determination of the methanol tolerance; incubation with increasing methanol concentrations, with constant coating and constant ligand concentration (VASP); up to a concentration of 25%, methanol has virtually no effect on the assay.
Figure 3B:
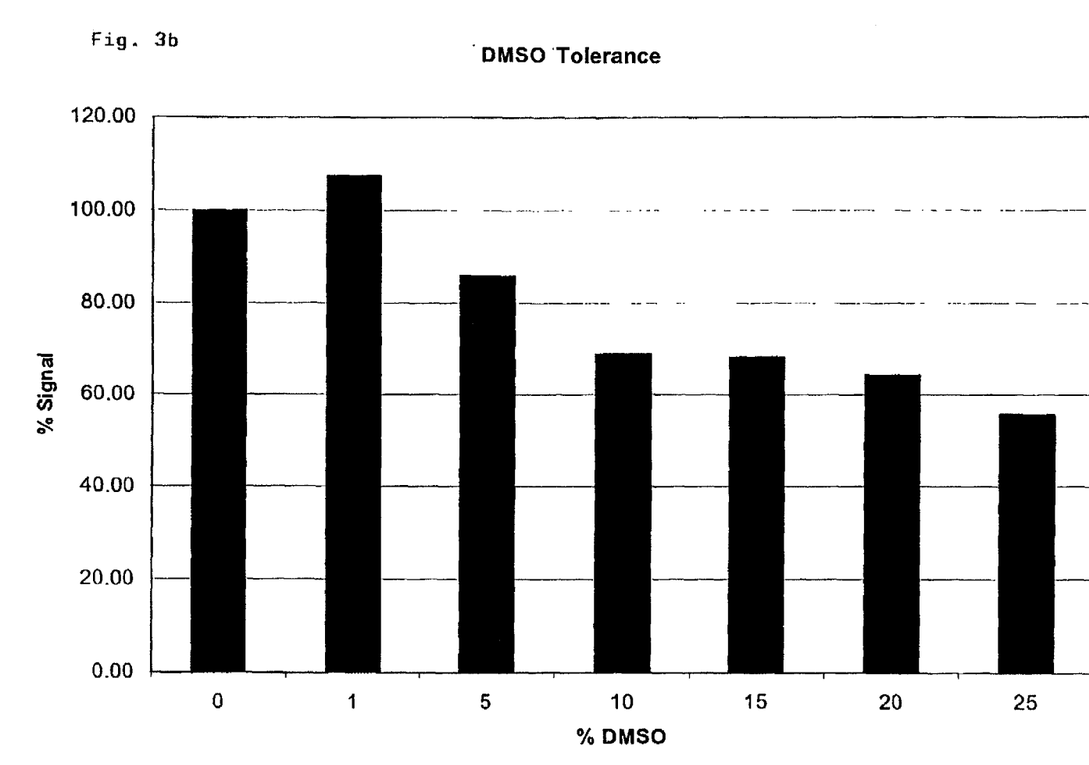
FIG. 3b: Determination of the DMSO tolerance; incubation with increasing concentrations of DMSO at constant coating and constant ligand concentration (VASP); at 25%, DMSO reduces the signal by almost half.

To ensure that the assay can be used for HTS, the assay has to be sufficiently tolerant to the standard solvents of the substance libraries. In general, these standard solvents are dimethyl sulfoxide (DMSO) and methanol. To test the tolerance of the assay to these two solvents, the incubations (with constant coating and constant ligand concentration (VASP)) were carried out using increasing concentrations of methanol and DMSO. It was found that, up to a concentration of 25%, methanol had virtually no effect on the assay (FIG. 3a), whereas at 25% DMSO, the signal was reduced by almost half (FIG. 3b). However, at the DMSO concentrations of 1-5% which are customarily used in screening, the signal reduction was only up to 15%, which is acceptable for an HTS assay.

EXAMPLE 6

Miniaturization

In the manner described above, the assays were initially carried out in 96-well plates. Here, it was possible to reduce the assay volume from 100 µl per well to 50 µl.

For further miniaturization of the assay for use in HTS, the assay was adapted to 384-well plates. For this purpose, 384-well plates of various manufacturers having different surfaces and colors were tested. Among the plates tested, the best values were found for the 384-well plates from Greiner. Here, white and black plates behaved in a very similar manner, even though the background for the black plates was particularly low. Among the surfaces tested (low binding, untreated, high binding), the best results were obtained for untreated surfaces.

By using 384-well plates, it was possible to reduce the assay volume further, to 20 µl per well. Fortunately, an additional effect of the miniaturization was a further improvement of the S/N ratio to about 100.

EXAMPLE 7

Chart: Assay Protocol (for 384-well Plates)

| 1. | Coating of the plates: GST-zyxin(1-142) in PBS 5 µg/ml | 20 µl | 1 hr RT |
|---|---|---|---|
| 2. | Blocking 15% BSA in PBS | 100 µl | 1 hr RT |
| 3. | Washing PBS | 3 × 100 µl | |
| 4. | Incubation with VASP VASP in DELFIA assay buffer 5 µg/ml | 20 µl | 1 hr RT |
| 5. | Washing PBS | 3 × 100 µl | |
| 6. | Detection α-VASP (IE273): 1.25 µg/ml α-mouse-Eu(N1): 50 ng/ml in DELFIA assay buffer | 20 µl | 1 hr RT |
| 7. | Washing DELFIA wash buffer | 3 × 100 µl | |
| 8. | Enhancement DELFIA enhancement solution | 50 µl | 15 min. |

EXAMPLE 8

Homogeneous Assay Using Energy Transfer of Fluorescently Labeled VASP and Zyxin or a Zyxin Derivative For the homogenous assay, human VASP having a complete amino acid sequence, isolated from insect cells (SF21), was used. The binding of specific antibodies to the VASP provided a fluorescent label. The binding partners used initially were peptides having the VASP binding motif FPPPP (SEQ. ID. NO. 1) which were likewise capable of binding to the other fluorophor for the energy transfer through coupled biotin (streptavidin-APC). However, in subsequent experiments, the VASP binding partner used was, instead of peptides, a GST fusion protein with the N-terminus of zyxin (GST-zyxin(1-142)) which contained several of these FPPPP (SEQ. ID. NO. 1) motifs. To this end, GST-zyxin(1-142) was expressed in $E.\ coil$, purified, and covalently modified with biotins. Thus, it was possible to measure a transfer of energy between the fluorescently labeled binding partners.

---

What is claimed is:

1. A process for identifying a chemical compound for possible use in a medicament for treating a disorder selected from the group consisting of a cardiovascular disorder, an inflammatory disorder, and a disorder of blood vessels said compound modulating an interaction between i) a human EVH1 (Ena-VASP—(*Drosophilia melanogaster* enabled vasodilator-stimulated phosphoprotein)—Homology 1) binding domain or a protein having a human EVH1 binding domain and ii) a human EVH1 domain or a protein having a human EVH1 domain, which process comprises:
   a) bringing a human EVH1 binding domain or a protein having a human EVH1 binding domain which interacts with a human EVH1 domain or a protein having a human EVH1 domain into contact with a chemical compound to be examined on a surface which consists of a solid body and is coated with a human EVH1 binding domain or a protein having a human EVH1 binding domain;
   b) incubating the mixture according to a) with a monoclonal antibody selected from the group consisting of mAB IE245 and mAB IE273 said antibody specifically binding to a human EVH1 binding domain or a protein having a human EVH1 binding domain or a human EVH1 domain or a protein having a human EVH1 domain or which has an antigen which is fused with or chemically coupled to these domains or proteins;
   c) incubating the mixture according to b) with a second antibody which is capable of specifically binding the antibody from mixture b), said second antibody having an attached label that can be detected biochemically or physicochemically;
   d) detecting the label on the second antibody after incubation according to c) by biochemical or physicochemical detection; and
   e) identifying the chemical compound thereby detected as a potential medicament for treating a disorder selected from the group consisting of a cardiovascular disorder, an inflammatory disorder, and a disorder of blood vessels.

2. A process for identifying a chemical compound for possible use in a medicament for treating a disorder selected from the group consisting of a cardiovascular disorder, an inflammatory disorder, and a disorder of blood vessels said compound modulating an interaction between a human EVH1 (Ena-VASP—(*Drosophilia melanogaster* enabled vasodilator-stimulated phosphoprotein)—Homology 1) binding domain or a protein having a human EVH1 binding domain and a human EVH1 domain or a protein having a human EVH1 domain, which process comprises:
   a) bringing a human EVH1 binding domain or a protein having a human EVH1 binding domain which interacts with a human EVH1 domain or a protein having a human EVH1 domain into contact with a chemical compound to be examined;
   b) incubating the mixture according to a) with a monoclonal antibody selected from the group consisting of mAB IE245 and mAB IE273 said antibody specifically binding to a human EVH1 binding domain or a protein having a human EVH1 binding domain or a human EVH1 domain or a protein having a human EVH1 domain or which has an antigen which is fused with or chemically coupled to these domains or proteins;
   c) incubating the mixture according to b) with a second antibody which is capable of specifically binding the antibody from mixture b), said second antibody having an attached label that can be detected biochemically or physicochemically;
   d) detecting the label on the second antibody after incubation according to c) by biochemical or physicochemical detection; and
   e) identifying the chemical compound detected as a potential medicament for treating a disorder selected from the group consisting of a cardiovascular disorder, an inflammatory disorder, and a disorder of blood vessels;
   wherein step a) takes place on a solid body, said solid body being coated with a human EVH1 domain or a protein having a human EVH1 domain, the human EVH1 domain or the protein having the human EVH1 domain on said solid body interacting with a human EVH1 binding domain or a protein having a human EVH1 binding domain.

3. The process as claimed in claim 1 or 2, wherein the solid body forms part of a microtiter plate.

4. The process as claimed in claim 1 or 2, wherein the protein having a human EVH1 domain used is VASP (vasodilator-stimulated phosphoprotein) or a fusion protein comprising: i) a first fusion component selected from the group consisting of a VASP and a VASP fragment having an EVH1 domain, and ii) a second fusion component selected from the group consisting of a glutathione S-transferase, a maltose binding protein and a hexahistidine.

5. The process as claimed in claim 1 or 2, wherein the zyxin derivative comprises a fusion protein which consists essentially of: i) a first fusion component selected from the group consisting of zyxin and a zyxin fragment having a human EVH1 binding domain and i) a second fusion component selected from the group consisting of a glutathione S-transferase and a maltose binding protein.

6. The process as claimed in claim 5, wherein the protein having a human EVH1 binding domain is zyxin or a zyxin derivative consisting of a fusion protein of glutathione S-transferase having the first 142 amino acids of zyxin fused to the C-terminus of said glutathione S-transferase.

7. The process as claimed in claim 1 or 2, wherein the monoclonal antibody is mAB IE245.

8. The process as claimed in claim 1 or 2, wherein the monoclonal antibody is mAB IE273.

9. The process as claimed in claim 1 or 2, wherein the biochemically or physiochemically detectable antibody label of step c) is a radioactive isotope, a fluorescent dye, or an enzyme is used for the incubation according to c).

10. The process as claimed in claim 9, wherein the enzyme is alkaline phosphatase or β-galactosidase.

11. The process as claimed in claim 9, wherein the fluorescent dye is a lanthanide complex.

12. The process as claimed in claim 11, wherein the lanthanide complex used is a europium complex.

13. The process as claimed in claim 1 or 2, wherein the EVH1 domain or protein having a human EVH1 domain is recombinantly prepared in insect cells.

14. The process as claimed in claim 13, wherein the protein having a human EVH1 domain is VASP or a VASP fragment having the EVH1 domain.

* * * * *

UNITED STATES PATENT AND TRADEMARK OFFICE
CERTIFICATE OF CORRECTION

| | | |
|---|---|---|
| PATENT NO. | : 7,563,582 B2 | Page 1 of 1 |
| APPLICATION NO. | : 09/989188 | |
| DATED | : July 21, 2009 | |
| INVENTOR(S) | : Jordan et al. | |

It is certified that error appears in the above-identified patent and that said Letters Patent is hereby corrected as shown below:

On the Title Page

Item [*] Notice: Subject to any disclaimer, the term of this patent is extended or adjusted under 35 USC 154(b) by 510 days.

Delete the phrase "by 510 days" and insert -- by 1068 days --

Signed and Sealed this

Fourth Day of May, 2010

David J. Kappos
*Director of the United States Patent and Trademark Office*

UNITED STATES PATENT AND TRADEMARK OFFICE
CERTIFICATE OF CORRECTION

PATENT NO. : 7,563,582 B2
APPLICATION NO. : 09/989188
DATED : July 21, 2009
INVENTOR(S) : Jordan et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1177 days.

Signed and Sealed this

Fourteenth Day of December, 2010

David J. Kappos
*Director of the United States Patent and Trademark Office*